United States Patent [19]

Korteweg

[11] Patent Number: 4,952,204
[45] Date of Patent: Aug. 28, 1990

[54] DRY HANDLE SWAB ASSEMBLY AND UNIT

[75] Inventor: Wayne Korteweg, Ledyard, Conn.

[73] Assignee: GAM-MED Packaging Corporation, Antioch, Ill.

[21] Appl. No.: 230,511

[22] Filed: Aug. 10, 1988

[51] Int. Cl.$^5$ ............................................. A61M 35/00
[52] U.S. Cl. ........................................ 604/1; 128/759; 206/363
[58] Field of Search ........................................ 604/1-3; 128/749, 759; 401/132, 196; 206/210, 363

[56] References Cited

U.S. PATENT DOCUMENTS

| | | |
|---|---|---|
| 1,146,522 | 7/1915 | Robert . |
| 1,166,761 | 1/1916 | Higgins . |
| 1,221,227 | 4/1917 | Schulz . |
| 1,229,195 | 6/1917 | Hamilton . |
| 1,309,201 | 7/1919 | Hollister . |
| 1,573,648 | 2/1926 | Sheely . |
| 2,902,146 | 9/1959 | Doherty ............................ 206/63.2 |
| 3,163,160 | 12/1964 | Cohen . |
| 3,513,830 | 5/1970 | Kalayian . |
| 3,614,245 | 10/1971 | Schwartzman ..................... 401/132 |
| 3,640,268 | 2/1972 | Davis . |
| 3,759,259 | 9/1973 | Truhan . |
| 3,774,609 | 11/1973 | Schwartzman . |
| 3,776,220 | 12/1973 | Monaghan . |
| 3,847,151 | 11/1974 | D'Alessandro et al. . |
| 3,958,571 | 5/1976 | Bennington . |
| 4,218,155 | 8/1980 | Weidner ............................ 401/132 |
| 4,432,749 | 2/1984 | Snyder et al. ..................... 604/2 |
| 4,586,604 | 5/1986 | Alter ................................. 604/1 |
| 4,749,655 | 6/1988 | Monthony et al. ................. 604/1 |

FOREIGN PATENT DOCUMENTS 647053 4/1964 Belgium .

Primary Examiner—Stephen C. Pellegrino
Attorney, Agent, or Firm—Stephen Weiss

[57] ABSTRACT

A swab, and a substance to be applied thereby, are contained within a sleeve which can readily be opened by use of manual force. The sleeve provides a handle portion that conforms closely to that of the swab stick, thus offering a secure and natural grip for manipulation of the swab while, at the same time, minimizing the amount of the contained substance that can seep along the length of stick, and an element of the sleeve that remains after opening of the unit also serves a protective function. Because of the form of the sleeve it is easy and inexpensive to fabricate as a fully functional article, using only an internal mold member, and it lends itself to facile assembly with the swab.

23 Claims, 3 Drawing Sheets

DRY HANDLE SWAB ASSEMBLY AND UNIT

BACKGROUND OF THE INVENTION

Swabs, consisting of a stick-like handle and a bud of cotton or other absorbent or porous material at one end, are of course in widespread use, particularly as applicators for medicinal, cleaning, and cosmetic liquids. A demand exists for a self-contained unit consisting of a swab prepackaged with the substance for which it is to be used, due to the convenience and sanitation benefits that are afforded thereby.

Swabs and the like in closed containers have heretofore been provided, in some instances also including a liquid substance. For example, Doherty U.S. Pat. No. 2,902,146, issued Sept. 1, 1959, provides a sterile package in which a surgical swab, contained in an interior sac, is sealed within a casing. Monaghan U.S. Pat. No. 3,776,220, issued Dec. 4, 1973, provides a unit in which a diagnostic swab and a culture medium are both contained within different sections of the same plastic tube, the two sections being separated by a frangible seal.

Swab-like implements enclosed within various forms of containers are also disclosed in Robert U.S. Pat. No. 1,146,522, issued July 13, 1915, Sheely U.S. Pat. No. 1,573,648, issued Feb. 16, 1926, Cohen U.S. Pat. No. 3,163,160, issued Dec. 29, 1964, Kalayjian U.S. Pat. No. 3,513,830, issued May 26, 1970, and Davis U.S. Pat. No. 3,640,268, issued Feb. 8, 1972. Various forms of applicators, associated with supply reservoirs, are shown in Higgins U.S. Pat. No. 1,166,761, issued Jan. 4, 1916, Schulz U.S. Pat. No. 1,221,227, issued Apr. 3, 1917, Hollister U.S. Pat. No. 1,309,201, issued July 8, 1919, Schwartzman U.S. Pat. No. 3,614,245, issued Oct. 19, 1971, Truhan U.S. Pat. No. 3,759,259, issued Sept. 18, 1973, Schwartzman U.S. Pat. No. 3,774,609, issued Nov. 27, 1973, D'Alessandro et al U.S. Pat. No. 3,847,151, issued Nov. 12, 1974, Bennington U.S. Pat. No. 3,958,571, issued May 25, 1976 and Snyder et al U.S. Pat. No. 4,432,749, issued Feb. 21, 1984.

Despite the level of activity in the art evidenced by the foregoing, a need exists for a prepackaged unit, including an enclosed swab and a substance for application, which is neat and convenient to handle and use, and relatively facile, simple and inexpensive to produce.

Accordingly, it is the broad object of the present invention to provide a novel unit, including a swab and a substance contained within a plastic sleeve, and to provide a novel sleeve and swab assembly for producing the same, which is neat and convenient to handle and use, and relatively facile, simple and inexpensive to produce.

It is a more specific object of the invention to provide such a unit and assembly wherein the sleeve provides an enclosure that is secure but nevertheless readily opened by manual force, and that also provides an integral element for shielding the user's hand from the contained substance and for curbing contact of the area being treated.

Another more specific object is to provide such a unit and assembly in which the sleeve is constructed to afford a secure and natural-feeling grip, for manipulation of the assembled swab, and to show evidence of tampering.

SUMMARY OF THE INVENTION

It has now been found that certain of the foregoing and related objects of the invention are attained by the provision of a sealable assembly comprising a swab having an elongated, small diameter stick with an applicator element at one end thereof, and an elongated, thin-wall hollow sleeve assembled with the swab. The sleeve is integrally formed, as a single piece, from a relatively rigid plastic material that is manually compressible and severable in thin sections, and it has a handle portion at one end, a receptacle portion at the other end, and a transition portion therebetween. The handle portion, which includes an element that frictionally engages the free end of the stick, extends along a major part of its length. It conforms generally to the stick, but is spaced slightly from the surface thereof throughout most of the coextensive length, to provide sufficient clearance for facile assembly while minimizing the gap therebetween. The cross section of the receptacle portion is substantially larger than is that of the handle portion of the sleeve, and the adjacent components at the intersection between the receptacle and transition portions are so configured that compression of the sleeve thereat will create a significant level of stress, thereby facilitating manual severance of the sleeve. Because of the relative lengths of the stick and the handle portion, the applicator element of the swab will be contained, at least substantially, within the receptacle portion of the sleeve.

In the preferred embodiments, the component of the transition portion that is disposed at the intersection with the receptacle portion will be of substantially annular configuration, and most desirably the adjacent components at the intersection will either be mutually perpendicular or disposed with an acute interior angle between them. In especially preferred embodiments, the transition portion will be of compound configuration and will include a cylindrical component directly adjacent the annular component.

Generally, the receptacle portion of the sleeve will be cylindrical and will have a diameter that is more than about triple that of the handle portion thereof; a short tip component at the free end of the handle portion, of smaller diameter than the remainder thereof, will advantageously provide the stick-engaging element. Typically, the swab will be about 11 centimeters in length; the sleeve handle portion will be about 6 centimeters long and less than about 0.5 centimeter in diameter, and its receptacle portion and an adjacent cylindrical component of the transition portion thereof will have diameters of about 1.3 and 1.15 centimeters, respectively, with the cylindrical component being at least about 0.13 centimeter long. When the plastic material employed for fabrication of the sleeve is polypropylene, it will desirably have a substantially uniform thickness of approximately 0.3 millimeter.

Other objects of the invention are attained by the provision of a swab or applicator unit, including an applicator assembly as hereinabove described, and a contained substance. The substance will normally be a liquid, and it will be confined substantially within the receptacle and transition portions of the sleeve, the latter being closed at the free end of its receptacle portion for that purpose.

DETAILED DESCRIPTION OF THE ILLUSTRATED EMBODIMENTS

Figure 1:
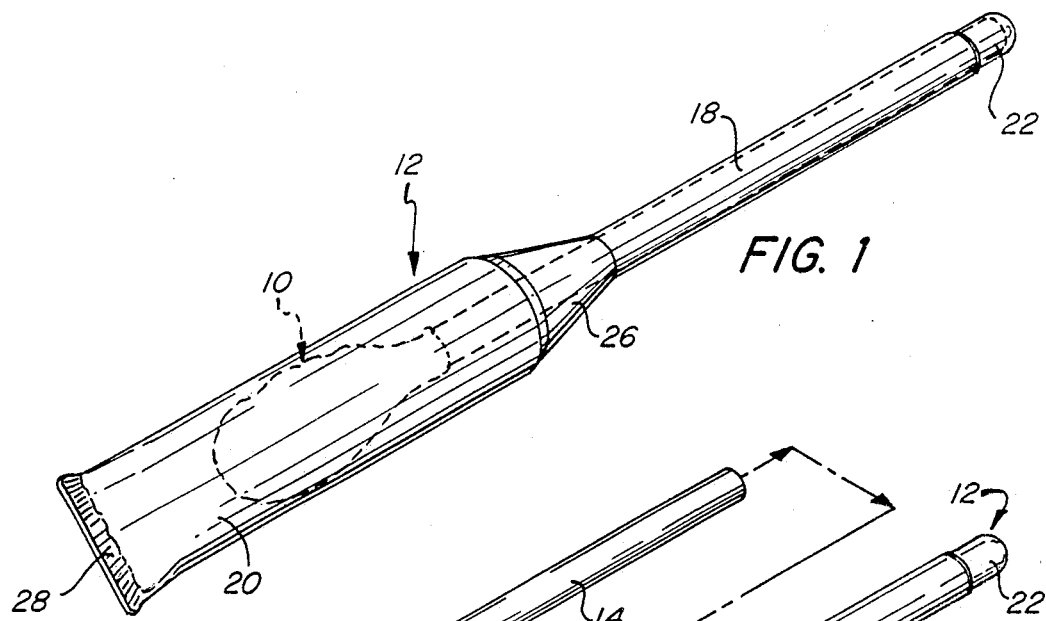
FIG. 1 is a perspective view of a self-contained swab unit embodying the present invention, the enclosed swab being shown in dotted line.

Turning now in detail to FIGS. 1-4 of the appended drawings, therein illustrated is a self-contained swab unit embodying the invention, and consisting of a swab, generally designated by the numeral 10, and a sleeve generally designated by the numeral 12. The swab 10 consists of a straight hollow plastic stick 14, with a bud 16 of cotton attached on one end.

The sleeve 12 is of circular cross section and hollow along its entire length, and is fabricated from a plastic material. It consists of a relatively small diameter cylindrical handle portion 18 at one end, a substantially larger diameter receptacle portion 20 at the opposite end, and a transition portion of compound configuration therebetween. The tip element 22 on the handle portion 18 has a diameter slightly reduced from that of the remainder of the handle portion, and serves to frictionally engage the tip of the swab stick 14.

Figure 2:
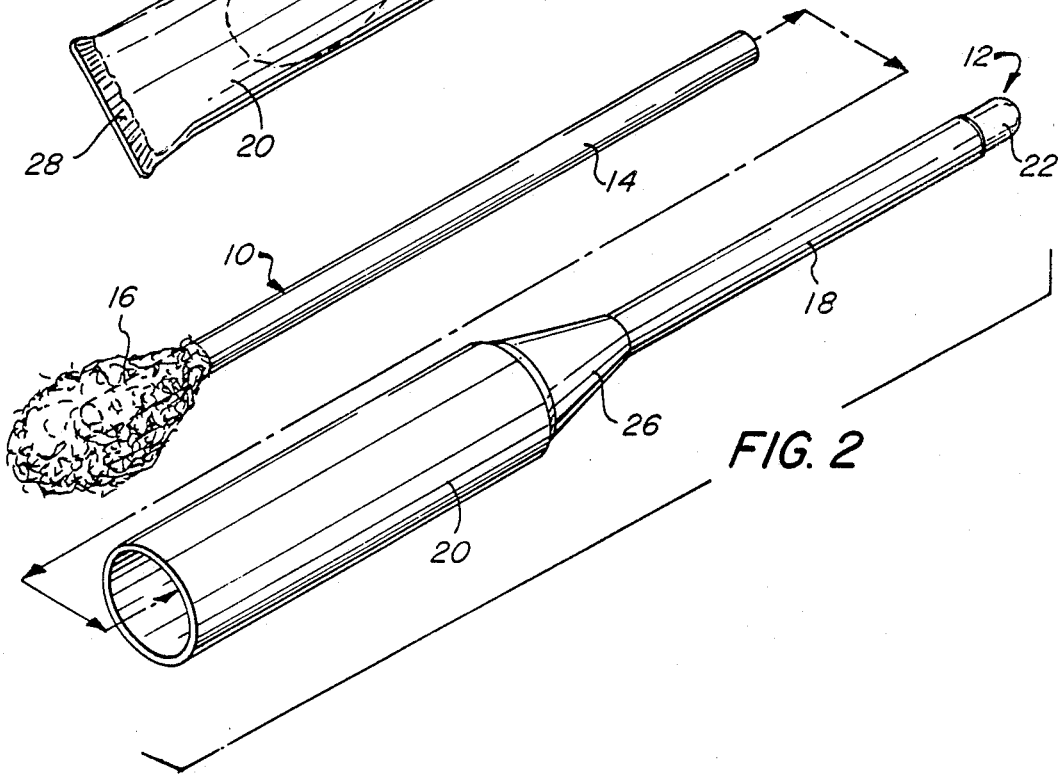
FIG. 2 is an exploded perspective view showing the swab and sleeve of the assembly of which the unit of FIG. 1 is comprised.
Figure 3:
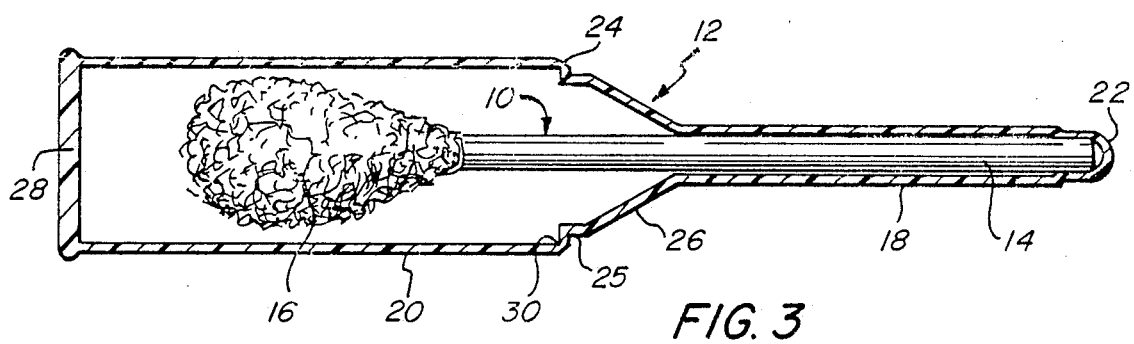
FIG. 3 is an elevational view of the unit of FIG. 1, with the sleeve shown in section.

As will be appreciated from FIG. 2, the assembly is produced simply by inserting the swab 10 into the sleeve 12 sufficiently to enable the element 22 to frictionally engage the stick 14, whereupon the bud 16 will reside within the enlarged receptacle portion 20. It will also be noted that the handle portion 18 conforms closely to the stick 14, albeit with a small gap (typically of about one millimeter) between their confronting surfaces throughout most of their coextensive lengths, to facilitate insertion of the swab. After assembly, the sleeve will normally be at least partially filled with a medicinal, cosmetic, or like substance, following which the sleeve will be closed, such as by a heat seal 28, to produce a sanitary, integral unit.

Figure 4:
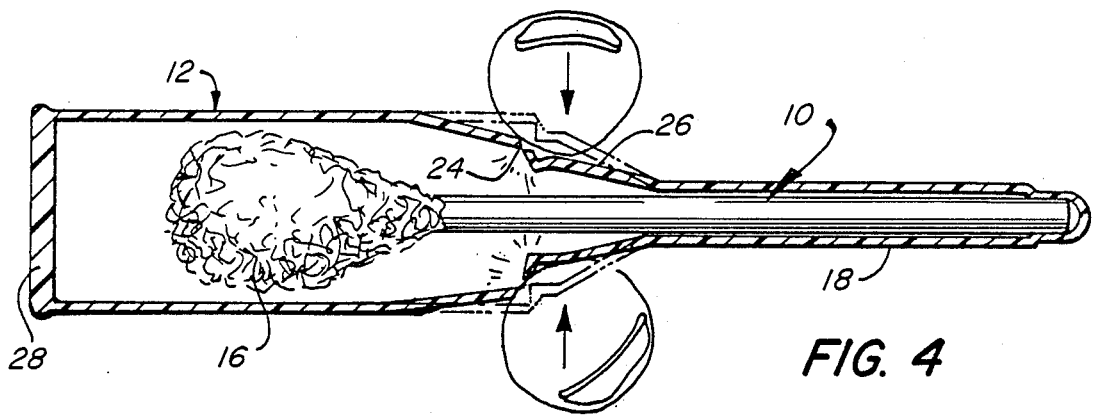
FIG. 4 is a view similar to FIG. 3, showing the sleeve being fractured under manual pressure.

Access to the swab is gained simply by squeezing the sleeve at the intersection between its receptacle and transition portions, as indicated in FIG. 4. The transition portion is uniquely configured to coact with the receptacle portion, so as to enable ready fracture under the influence of such force. In addition to affording access, this characteristic will provide a tamper-resisting feature to the package, since any loss of integrity will tend to be evident as cracking, crazing, or opacity at stress points.

The transition portion consists, more particularly, of a narrow annular component 24, a short cylindrical component 25, and a frustoconical component 26, the latter merging into the handle portion 18. The annular component 24 in turn connects to the receptacle portion 20, with the adjacent components forming a sharp interior right angle intersection at 30. As will be noted, however, the corresponding exterior corner is not sharply defined, but rather is more in the nature of a rounded chamfer. This results from material flow, and is a natural consequence of the preferred molding method and tooling structure employed, as will be described more fully hereinbelow.

Figure 5:
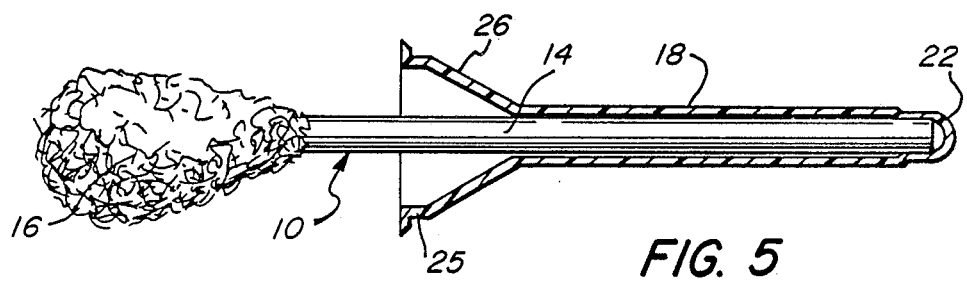
FIG. 5 is a view similar to FIG. 4, showing the receptacle portion of the sleeve removed.

In any event, the interior and exterior configurations together result in a minimum thickness of material at the intersection 30. Depending upon the nature of the material used to fabricate the sleeve, the stress created by compression (which arises because the adjacent components are incapable of assuming a compatible configuration upon flattening of the sleeve) will either cause it to snap at the intersection 30, or will at least crack or otherwise facilitate severance by a tearing action. As is seen in FIG. 5, the swab 10 is exposed for use upon removal of the receptacle portion.

The close conformity of the handle portion 18 of the sleeve to the stick 14 of the swab affords a secure and natural-feeling grip while, at the same time, minimizing the gap into which the contained substance can seep. The frustoconical component 26 of the transition portion, which remains after removal of the receptacle portion, provides means for limiting the location at which the assembly can be grasped, thus helping to prevent inadvertent touching of the area being treated, and it also serves to contain any of the substance that might drip, or run down the swab stick.

For best results, it has been found that a sleeve having dimensions such as those typified hereinabove will be fabricated from polypropylene, in a thickness of about 0.3 millimeter. This will afford a level of rigidity that will provide good handling and structural features while, at the same time, tending to produce fracture upon manual compression at the frangible joint.

Figure 10:
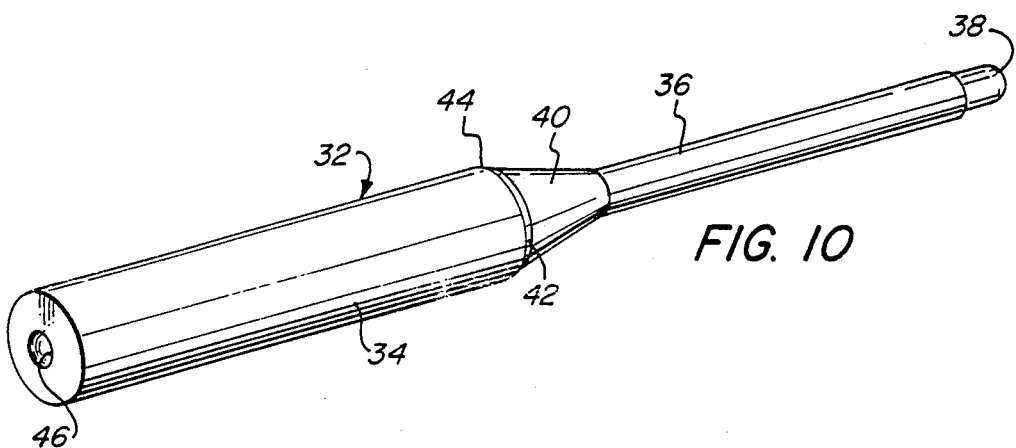
FIG. 10 is a perspective view showing a mold member suitable for use in producing the sleeve of FIGS. 1-5.

The preferred manner of producing the sleeve 12 is by fusion molding, utilizing a mold member such as that illustrated in FIG. 10 and generally designated by the numeral 32. Indeed, the sleeves hereof are specifically configured so as to permit fabrication (as fully functional articles) with such a mold member by that technique, and without need for any external tooling.

Since the configuration of the mold member must obviously match that of the sleeve, it need not be discussed in great detail. Suffice to say that it is desirably made of cold finished steel bar stock, polished to remove imperfections, and that it has a body portion 34, a handle portion 36 (with a reduced diameter tip element 38 thereon) and a transition portion therebetween consisting of a frustoconical component 40, a cylindrical component 42, and an annular component (not visible in this figure) spaced from the frustoconical component 40. It is important to note that the edge 44 adjacent to which the annular component lies is sharp and well defined, so as to produce the necessary desired degree of internal sharpness at the intersection 30, while at the same time inducing the material flow that will result in desired thinning thereat. A threaded bore 46 is provided in the larger end of the mold member, for mounting purposes.

As will be appreciated, to produce the sleeve the mold member 32 is heated to a temperature sufficient to provide the thermal energy necessary to melt the polymer, employed in finely divided particulate form. After solidification of the fused resin, it is merely a matter of stripping the article from the mold member; appropriate slight tapers built into the mold member, and other conventional practices for facilitating stripping, are known to those skilled in the art and may be employed as appropriate. It is of course necessary that no element of the mold member (and correspondingly, of the sleeve produced) be of greater extent, in a plane transverse to its longitudinal axis, than is any other element spaced further from the tip, since that would render stripping from the mold impossible, particularly in view of the degree of rigidity that the sleeve is to have for facile manual severance.

In this regard it must of course be appreciated that, if the plastic used is excessively rigid and brittle, the possibility of inadvertent fracture will exist. Furthermore, the resin must have a sufficiently low melt viscosity to permit coverage of all mold surfaces, and it must produce a nonporous and pinhole-free structure. Within the foregoing constraints, any of a variety of synthetic resinous materials may be utilized, and the selection thereof will be evident to those skilled in the art; nevertheless, exemplary thermoplastic resins that might be suggested are polypropylene, high density polyethylene, rigid polyvinyl chloride, and nylon, of which polypropylene will usually be preferred.

The swab assembly will normally be employed for the application of liquids to the body (e.g., for medicinal, disinfectant, cosmetic and cleaning purposes); however, the contained substance could as well be a powder, and a wide variety of nonpersonal applications, such as for application of lubricating oil to a mechanism, may occur to those skilled in the art. As used herein, therefore, the term "applicator" is to be broadly construed to include, for example, elements used primarily for removal of matter, as when the swab performs a cleaning function.

The range of sizes for the assembly and its components can also vary widely (e.g., the swab can be from about 3 to 15 centimeters in length, and the receptacle portion of the sleeve can be much longer or much shorter than the handle portion), as long as the wall thicknesses are controlled appropriately to afford the desired functional characteristics, as discussed herein. It is also important, for proper functioning (at least when the sleeve is of 0.3 millimeter thick polypropylene) that the component intersecting with the receptacle portion (e.g., the annular component 24 in the embodiment of FIGS. 1–5) be at least about 0.13 centimeter wide, to create adequate stress at the fracture point(s).

Figure 6:
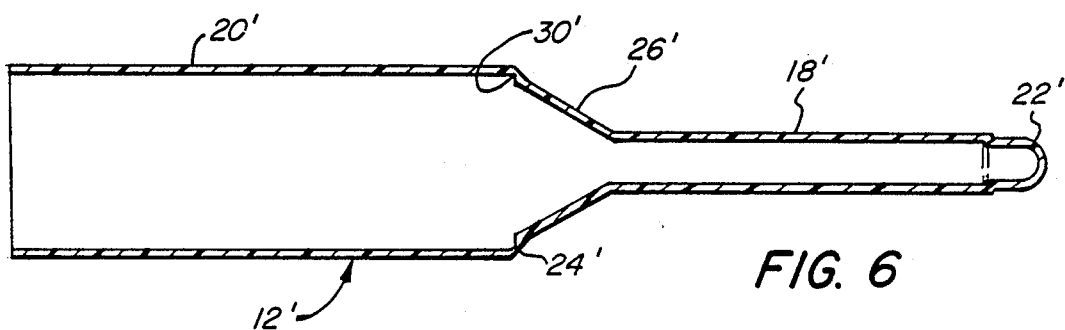
FIGS. 6-9 are sectional views showing other forms of sleeves suitable for use in the assembly and unit of the invention.

Turning now to FIG. 6, the sleeve illustrated is virtually the same as sleeve 12, except that its transition portion omits the short cylindrical component 25; primed numerals are therefore employed.

Figure 7:
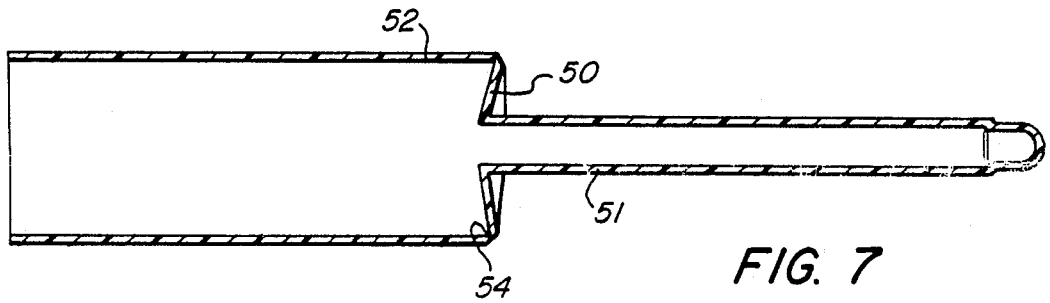

The transition portion of the sleeve of FIG. 7 is similar, but consists of an annular component 50 extending directly between the handle portion 51 and the end component 52 of the receptacle portion. In addition, the annular component 50 is disposed so as to form an acute interior angle with the component 52, thereby producing an intersection at 54 that is even sharper, internally, than is the intersection 30 of the sleeve embodiment of the earlier Figures.

Figure 8:
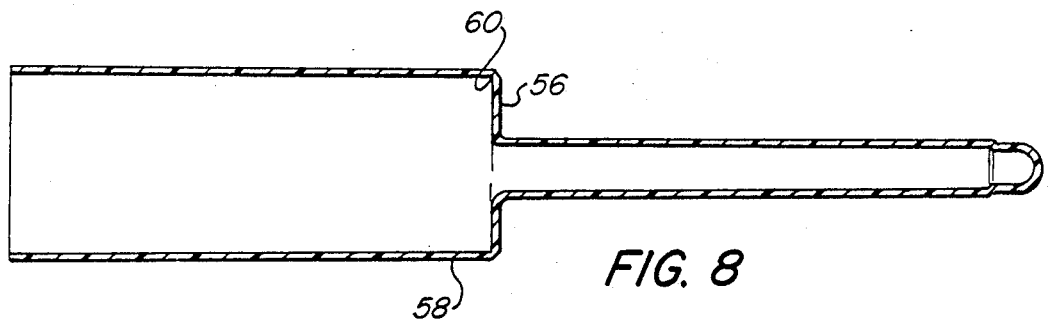

The sleeve of FIG. 8 is the same as that of FIG. 7, except that its annular component 56 forms a right-angle with the adjacent receptacle portion component 58, and a corresponding intersection at 60.

Figure 9:
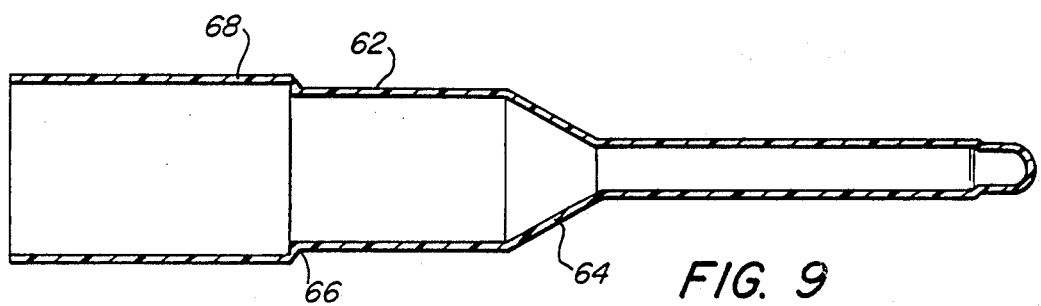

The form of sleeve shown in FIG. 9 is again similar to that of FIGS. 1–5, with the exception however that a relatively long cylindrical component 62 is interposed between the frustoconical component 64 and the annular component 66. Annular component 66 cooperates with components 62 and adjacent component 68 on the end of the receptacle portion in a manner that is wholly equivalent to the opening function cooperatively produced by the operative elements of the initially described embodiment.

It will of course be appreciated that mold members comparable to that of FIG. 10, but suitably modified, will preferably be used to produce the sleeves of FIGS. 6–9.

Thus, it can be seen that the present invention provides a novel unit, including a swab and a substance contained within a plastic sleeve, and a sleeve and swab assembly for producing the same, which is neat and convenient to handle and use, and is relatively facile, simple and inexpensive to produce. The sleeve provides an enclosure that is secure, but nevertheless readily opened by manual force, and it also provides an integral element for shielding the user's hand from the contained substance and for curbing contact with the area being treated; in addition, its construction affords a secure and natural-feeling grip for manipulation of the assembled swab.

Having described the invention, what is claimed is:

1. A sealable, manually openable applicator assembly comprising: a swab having an elongated, small diameter stick with an applicator element at one end thereof; and an elongated, thin-wall hollow sleeve assembled with said swab, said sleeve being integrally formed as a single piece from a relatively rigid plastic material that is manually compressible and severable in thin sections, and having a handle portion at one end, a receptacle portion at the other end, and a transition portion therebetween, said handle portion having an element frictionally engaging the other end of said stick, and said handle portion extending along a substantial part of the length of, and conforming to, said stick and being spaced slightly from the surface thereof, other than at said engaging element, to provide sufficient clearance for facile assembly while minimizing the gap therebetween, said receptacle portion being of substantially larger cross section than said handle portion, and the adjacent components of said receptacle and transition portions at the intersection therebetween cooperatively constituting means for creating stress in said sleeve, said adjacent components being so relatively configured as to assume incompatible configurations upon flattening of said sleeve, to thereby create a significant level of stress therebetween, compression of said sleeve thereat thereby facilitating manual severance of said sleeve at that location, the relative lengths of said stick and said handle portion being such that said applicator element of said swab is contained at least substantially within said receptacle portion of said sleeve.

2. The assembly of claim 1 wherein said component of said transition portion is of substantially annular configuration.

3. The assembly of claim 2 wherein said adjacent components are mutually perpendicular.

4. The assembly of claim 3 wherein said transition portion is of compound configuration, and includes a cylindrical component directly adjacent said substantially annular component.

5. The assembly of claim 4 wherein said receptacle portion is cylindrical, and wherein said receptacle portion and said cylindrical component of said transition portion have diameters of about 1.3 and 1.15 centimeters, respectively.

6. The assembly of claim 5 wherein the thickness of said sleeve wall has a substantially uniform value of approximately 0.3 millimeter, wherein said handle portion of said sleeve has a diameter of less than about 0.5 centimeter, and wherein said clearance has a value of less than about one millimeter.

7. The assembly of claim 6 wherein said handle portion and said stick are about 6 and 11 centimeters in length, respectively.

8. The assembly of claim 4 wherein said transition portion additionally includes a frustoconical component directly adjacent said cylindrical component and joined directly to said handle portion.

9. The assembly of claim 2 wherein said adjacent components are disposed with an acute interior angle therebetween.

10. The assembly of claim 2 wherein said receptacle portion of said sleeve is of cylindrical configuration, and wherein said component of said transition portion is at least 0.13 centimeter wide.

11. The assembly of claim 10 wherein the diameter of said handle portion of said sleeve is less than about one-third the diameter of said receptacle portion thereof, and wherein said handle portion is coextensive with said stick along a major part of the length of said stick.

12. The assembly of claim 11 wherein said handle portion diameter is less than about 0.5 centimeter.

13. The assembly of claim 12 wherein said receptacle portion diameter is about 1.3 centimeters.

14. The assembly of claim 1 wherein said handle portion has a short tip component at its free end, which is of slightly smaller diameter than is the remainder thereof and which provides said engaging element.

15. The assembly of claim 1 wherein the thickness of said sleeve wall has a substantially uniform value of approximately 0.3 millimeter, and wherein said plastic material is polypropylene.

16. The assembly of claim 1 wherein said sleeve is closed at said one end and open at said other end, and wherein no element that is closer to said one end than is any other element is of larger cross-sectional dimension than said other element.

17. An applicator unit for a substance, including:
a swab having an elongated, small diameter stick with an applicator element at one end thereof;
an elongated, thin-wall hollow sleeve assembled with said swab, said sleeve being integrally formed as a single piece from a relatively rigid plastic material that is manually compressible and severable in thin sections, and having a handle portion at one end, a receptacle portion at the other end, and a transition portion therebetween, said handle portion having an element frictionally engaging the other end of said stick, and said handle portion extending along a substantial part of the length of, and conforming to, said stick and being spaced slightly from the surface thereof, other than at said engaging element, to provide sufficient clearance for facile assembly while minimizing the gap therebetween, said receptacle portion being of substantially larger cross section than said handle portion, and the adjacent components of said receptacle and transition portions at the intersection therebetween cooperatively constituting means for creating stress in said sleeve, said adjacent components being so relatively configured as to assume incompatible configurations upon flattening of said sleeve, to thereby create a significant level of stress therebetween, compression of said sleeve thereat thereby facilitating manual severance of said sleeve at that location, the relative lengths of said stick and said handle portion being such that said applicator element of said swab is contained at least substantially within said receptacle portion of said sleeve; and
a substance contained within said receptacle and transition portions of said sleeve, said sleeve being closed at the free end of said receptacle portion thereof.

18. The unit of claim 17 wherein said receptacle portion of said sleeve is of cylindrical configuration, wherein said transition portion is of compound configuration and includes a substantially annular component and a cylindrical component directly adjacent thereto, and wherein said adjacent components are mutually perpendicular or are disposed with an acute interior angle between them.

19. The unit of claim 18 wherein said receptacle portion and said cylindrical component of said transition portion have diameters of about 1.3 and 1.15 centimeters, respectively, and wherein the thickness of said sleeve wall has a substantially uniform value of approximately 0.3 millimeter.

20. The unit of claim 19 wherein said handle portion of said sleeve has a short tip component at its free end, which is of slightly smaller diameter than is the remainder thereof and which provides said engaging element, and wherein no element of said sleeve that is closer to said one end than is any other element thereof is of larger cross-sectional dimension than said other element.

21. The assembly of claim 19 wherein said handle portion diameter is less than about 0.5 centimeter, wherein said clearance has a value of about one millimeter, and wherein said substance is of liquid form.

22. The assembly of claim 21 wherein said receptacle portion diameter is about 1.3 centimeters, wherein said handle portion and stick are about 6 and 11 centimeters in length, respectively, and wherein said handle portion is coextensive with said stick along a major part of the length of said stick.

23. The assembly of claim 17 wherein the thickness of said sleeve wall has a substantially uniform value of approximately 0.3 millimeter, wherein said plastic material is polypropylene, and wherein said component of said transition portion is at least about 0.13 centimeter wide.

* * * * *